United States Patent
Blair et al.

[11] Patent Number: 5,825,845
[45] Date of Patent: Oct. 20, 1998

[54] PROTON BEAM DIGITAL IMAGING SYSTEM

[75] Inventors: Mark S. Blair, Madison, Wis.; David A. Lesyna, Redlands, Calif.; Pengyue James Lin, Riverside, Calif.; Jagadish P. Samantarai, Moreno Valley, Calif.; Berry B. Yeldell, Yorba Linda, Calif.

[73] Assignee: Loma Linda University Medical Center, Loma Linda, Calif.

[21] Appl. No.: 739,512

[22] Filed: Oct. 28, 1996

[51] Int. Cl.⁶ .................................................. A61N 5/10
[52] U.S. Cl. ............................................... 378/62; 378/65
[58] Field of Search ................................... 378/62, 63, 64, 378/65, 205

[56] References Cited

U.S. PATENT DOCUMENTS

| | | | |
|---|---|---|---|
| 4,917,344 | 4/1990 | Prechter et al. | 248/664 |
| 5,039,057 | 8/1991 | Prechter et al. | 248/664 |
| 5,039,867 | 8/1991 | Nishihara et al. | 378/205 |
| 5,117,829 | 6/1992 | Miller et al. | 128/653.1 |
| 5,297,037 | 3/1994 | Ifuku | 364/413.15 |

FOREIGN PATENT DOCUMENTS

| | | |
|---|---|---|
| 0480035A1 | 4/1992 | European Pat. Off. . |
| 0673661A2 | 9/1995 | European Pat. Off. . |

OTHER PUBLICATIONS

Hamilton, Russell J.; Kuchnir, Franca T.; Pelizarri, Charles A.; Sweeney, Patrick J.; Rubin, Steven J. "Repositioning accuracy of a noninvasive head fixation system for stereotactic radiotherapy", Med. Phys. 23(11) Nov. 1996, pp. 1909–1917.

*Primary Examiner*—Don Wong
*Attorney, Agent, or Firm*—Knobbe, Martens, Olson & Bear, LLP

[57] ABSTRACT

A proton beam digital imaging system comprising an X-ray source which is movable into the treatment beam line that can produce an X-ray beam through a region of the patient. An X-ray receiver receives the X-ray beam after it has passed through the patient and the X-ray receiver generates photons that correspond to the X-ray image. The photons are directed to a TEC CCD camera to produce a patient orientation image which displays the orientation of the center of the beam relative to selected monuments in the patient's skeletal structure. The system also receives a master prescription image which displays the target isocenter with respect to the same selected monuments of the patient's skeletal structure. By comparison of the relative positions of the center of the beam in the patient orientation image and the isocenter in the master prescription image with respect to the selected monuments, the amount and direction of movement of the patient to make the beam center correspond to the target isocenter is determined.

36 Claims, 9 Drawing Sheets

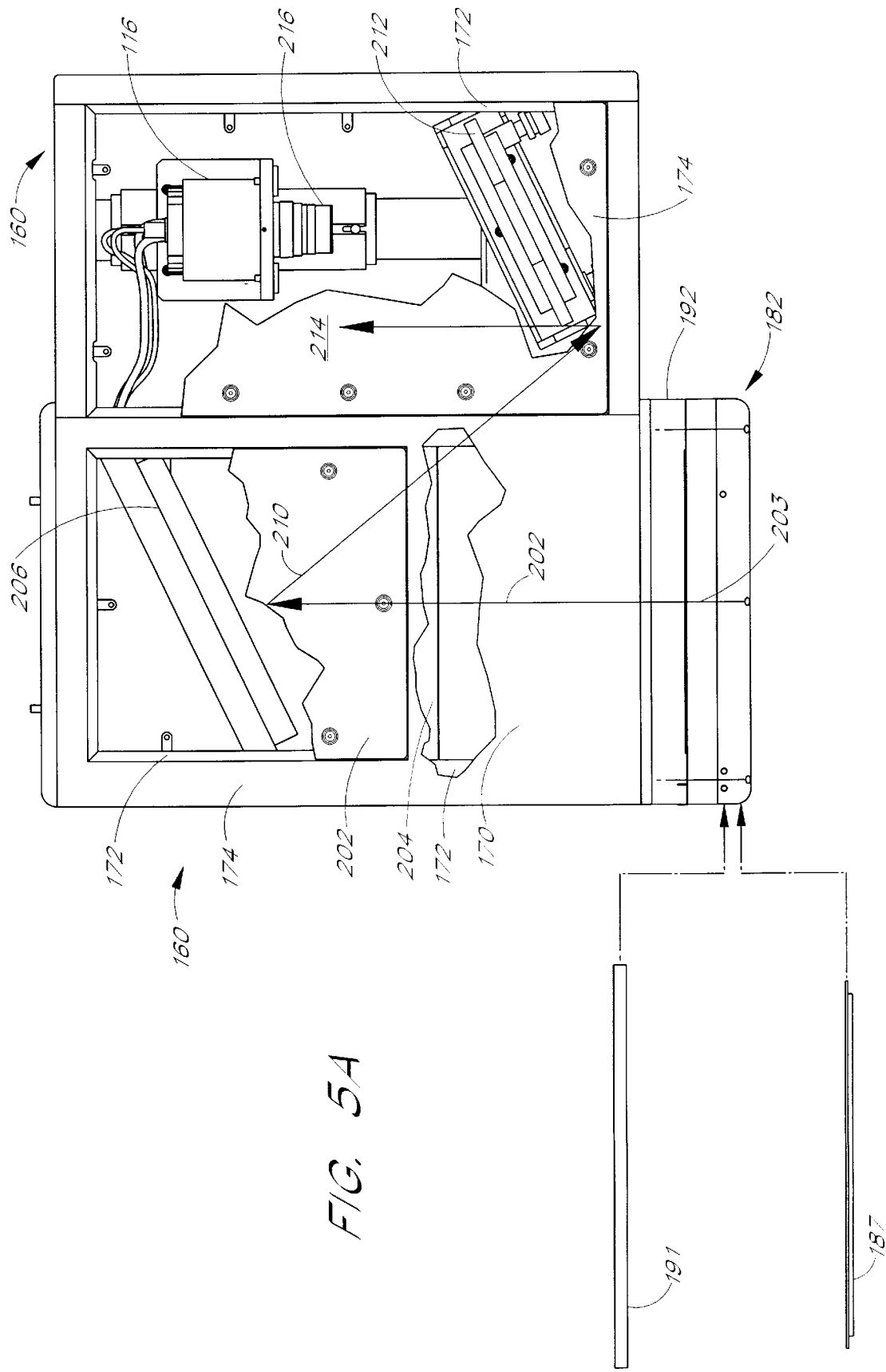

PROTON BEAM DIGITAL IMAGING SYSTEM

BACKGROUND OF THE INVENTION

1. Field of the Invention

The present invention relates to particle beam therapy systems and, in particular, concerns a digital imaging system for imaging a target region of a patient's body to determine the position of the patient relative to a particle beam delivery system to thereby allow the position of the patient to be adjusted into a desired position.

2. Description of the Related Art

Radiation particle therapy is commonly used to treat localized forms of cancer as well as other afflictions. Typically, an atomic particle, e.g., an electron, a proton, a neutron, or a sub-atomic particle, such as an X-ray, is emitted out of a nozzle towards a particular target region of the patient, often referred to as a target isocenter. The particle then collides with the cells within the target region of the patient and thereby damages these cells.

One particularly useful form of radiation therapy is proton beam therapy wherein protons are directed at a target isocenter located within a patient's body. Proton therapy has the advantage of the protons exhibiting a phenomena known as a Bragg peak wherein a substantial portion of the energy of the proton is released as the proton comes to a stop. Hence, by selecting the starting energy of the proton beam, the protons in the beam can be directed to come to a stop at the target isocenter thereby delivering a significant portion of their energy to the cells within the target isocenter. Proton therapy is currently in use at the Loma Linda University Medical Center located in Loma Linda, Calif., and the system used at the Loma Linda University Medical Center is described in greater detail in U.S. Pat. No. 4,870,287.

While proton therapy has significant clinical advantages over other types of therapy in particular instances, it also requires that the patient be accurately positioned with respect to the nozzle of the proton beam so that the proton beam is irradiating only the target isocenter. Otherwise, the proton beam could damage healthy cells within the patient's body. This is particularly important, for example, in treatments wherein the target isocenter is located within the brain of the patient. While accurately locating the patient with respect to a nozzle is very important in proton therapy, it is, of course, also very important in many other types of radiation therapy for similar reasons.

Typically, the patient who is receiving the proton therapy receives periodic treatments wherein the target isocenter is irradiated with the proton beam repeatedly over the course of an extended time period. For example, a patient may receive daily doses of proton radiation therapy over a month long period. Further, the target isocenter is often irradiated with a proton beam from a variety of different angles when the proton beam is delivered via a gantry system, such as the gantry system described in U.S. Pat. No. 4,917,344 and U.S. Pat. No. 5,039,057.

To ensure that the patient is accurately positioned with respect to the nozzle of the proton therapy beam, the position of the target isocenter is initially determined with respect to one or more monuments within the body of the patient. Generally, the monuments are comprised of points on the skeletal structure of the patient and the location of the target isocenter is then determined with respect to these monuments. One technique for determining the position of the target isocenter is to use a digitally reconstructed radiograph (DRR). Specifically, CT scans of the patients are taken using well-known techniques. These are assembled into the DRR and the location of the target isocenter, containing the afflicted tissues, e.g., tumors and the like, is then marked on the DRR. The DRR files can then be assembled to show images of the target isocenter from a variety of different perspectives.

Subsequently, when the patient is positioned within a support, such as the support described in U.S. Pat. No. 4,905,267, and the support is positioned on a treatment platform within the gantry structure of the proton treatment facility, an X-ray source is then positioned within the proton beam path and an X-ray receiver is positioned along the proton beam path on the opposite side of the patient. Hence, the X-ray source and X-ray receiver produce a photographic X-ray image of the region of the patient's body that is positioned within the path of the proton beam that will exit the nozzle of the proton beam delivery system. The center of the beam in the photographic X-ray image can then be determined with respect to the preselected monuments in the patient's body.

A comparison of the offset of the target isocenter from the preselected monuments in the DRR and the offset of the X-ray beam center from the same preselected monuments in the photographic X-ray image provides an indication of direction that the patient must be moved with respect to the nozzle so that the nozzle is centered at the target isocenter. Generally, this process is performed iteratively until the patient is in the correct alignment with respect to the nozzle of the proton delivery system. Further, this process typically has to be repeated for each orientation of the nozzle with respect to the patient as the nozzle is rotated about the gantry.

It will be appreciated that obtaining a photographic X-ray image of the region of the patient's body is very time consuming as each photographic image must be developed. Further, once the image is developed, the treating physician must then make measurements on the X-ray image and compare these measurements to the DRR image to determine how to move the patient. Hence, the patient must sit in the support for extended periods of time waiting for the treating physician to correctly align the patient. Consequently, the treatment facility is capable of accommodating fewer patients as a result of the increased time required to perform the necessary steps to align the patient. Hence, there is a need for a system which obtains images of the position of a patient relative to the nozzle in a more efficient manner so that the time required to determine the position of the patient relative to the nozzle and perform the necessary movement of the patient to correctly align the patient is minimized.

In some applications of radiation therapy, digital images of the X-rays are captured which reduce the film processing time. For example, U.S. Pat. No. 5,039,867 discloses a system which obtains an X-ray television image of the body of the patient. However, the '867 patent is designed to be used in conjunction with ionized particle beams and heavy particle beams and also uses an image intensifier to intensify the television image of the X-ray. This type of system is not readily adaptable to proton therapy treatment as the use of an image intensifier would introduce image distortion and, therefore, errors into the calculation of patient position which would be unacceptable. Since the proton beams can have a significantly more harmful effect on tissue, it is important to very accurately locate the patient in front of the nozzle and, consequently, the errors introduced by an image intensifier would result in too many inaccuracies for use in a proton therapy system.

Hence, there is a need for a system which is capable of capturing a non-photographic image of the region of the patient's body in front of the nozzle of a proton delivery system. This system should be capable of accurately determining the region of the patient's body in front of the nozzle without introducing any errors into the determination. Further, this system should also be readily adaptable into a gantry system wherein the determination of the patient's body with respect to the nozzle can be performed regardless of the angular orientation of the nozzle about the patient.

SUMMARY OF THE INVENTION

The aforementioned needs are satisfied by the proton therapy system of the present invention which comprises a gantry, a nozzle that is positioned on the gantry from which a proton beam will emerge, a beam path which feeds the proton beam to the nozzle, a moveable X-ray source which can be positioned in the beam path and an X-ray receiver positioned so as to receive X-rays that have been produced by the X-ray source after these X-rays have passed through the patient. Preferably, both the X-ray source and the X-ray receiver are mounted on the gantry so that the X-ray source and the X-ray receiver can be used to produce an image of the region of the patient that is in the path of the proton beam regardless of the orientation of the nozzle with respect to the patient. Further, the X-ray receiver preferably produces a digital image of the region of the patient that is in front of the nozzle.

In one aspect of the invention, the system also includes a computer system which has one or more master prescription images of the target isocenter and several landmarks or monuments within the body of the patient. In the preferred embodiment, the master prescription image is produced using a Digitally Reconstructed Radiograph (DRR) and the prescribing physician can determine the location of the target isocenter with respect to one or more preselected monuments within the body of the patient. The digital X-ray image produced by the image receiver preferably shows the center of the beam superimposed against the skeletal structure of the patient. The landmarks or monuments that have been selected in the master prescription image are preferably landmarks on the skeletal structure which are also perceivable in the X-ray image. The system preferably allows the treating physician to identify the monuments on the X-ray image and then determine the spatial relation between the center of the beam to the monument. The spatial relation of the center of the beam with regards to the monuments is then compared to the spatial relation between the target isocenter and the very same monuments in the prescription master image. This comparison yields offset values which are indicative of how far the center of the beam is offset from the target isocenter within the patient. These values can then be used to move the patient so that the target isocenter is correctly oriented in the center of the beam.

Preferably, there is a master prescription image prepared for each of the angles of the gantry that the beam is to be directed at the patient. Since the X-ray source and X-ray receiver are attached to the gantry, the positioning image can be obtained whenever the gantry is moved to a new position and the offsets can be appropriately calculated.

In another aspect of the invention, the X-ray receiver is comprised of an apparatus that includes a fluorescing screen, which fluoresces in response to X-rays impinging on the screen, wherein the photons generated by the fluorescing screen are then directed along a compact path to a cooled digital capture device. In one embodiment the digital capture device is comprised of a CCD camera having a 512×512 pixel thinned CCD sensor with an attached thermal electric cooler. The cooler removes heat energy and thereby reduces the amount of noise produced by the camera so that the camera is capable of obtaining an X-ray image of the portion of the patient's body in the path of the beam from X-rays produced by a diagnostic quality X-ray tube that operates in the 30 kV to 150 kV energy range.

Hence, the system of the present invention obtains accurate digital images of the portion of the patient's body that is in front of the nozzle and allows for a calculation of how far the center of the beam is offset from the target isocenter in the patient's body thereby providing measurements which allow the patient to be reoriented with respect to the beam nozzle. These and other objects and advantages of the present invention will become more fully apparent from the following description taken in conjunction with the accompanying drawings.

BRIEF DESCRIPTION OF THE DRAWINGS

FIGS. 5A through 5E are detailed views which further illustrate the image capture device of FIG. 4;

DETAILED DESCRIPTION OF THE PREFERRED EMBODIMENT

Figure 1:
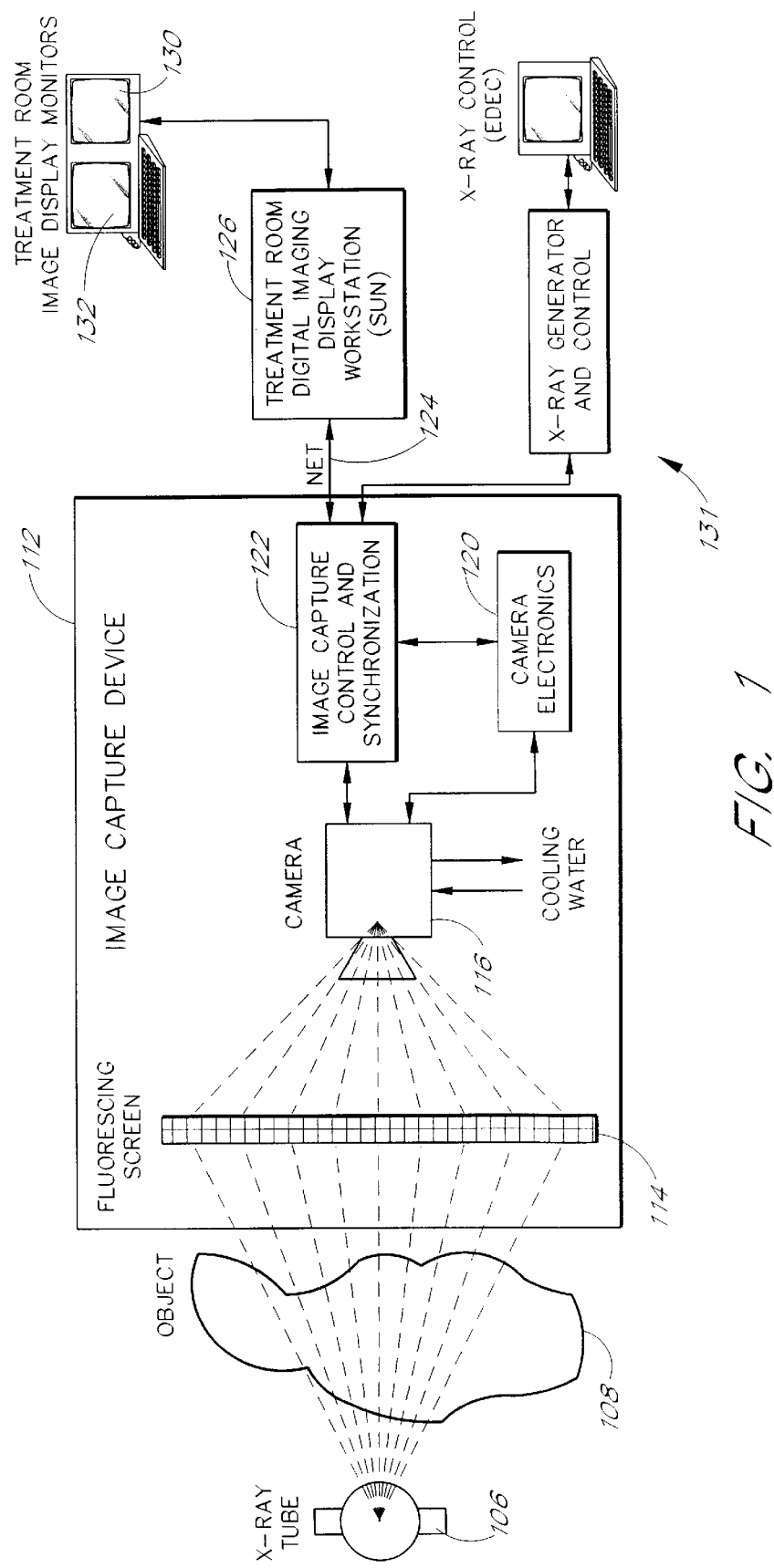
FIG. 1 is a block diagram of the digital imaging system of the preferred embodiment.

Reference will now be made to the drawings wherein like numerals refer to like parts throughout. FIG. 1 is a block diagram of a digital imaging system 100 of the preferred embodiment. The digital imaging system 100 is implemented on the proton beam delivery system 102 shown in FIG. 2. The proton beam delivery system 102 includes a gantry and corresponds to the proton beam delivery system described in U.S. Pat. No. 4,870,287 which is hereby incorporated by reference. Further, the structure of the gantry is as described in U.S. Pat. No. 4,917,344 and U.S. Pat. No. 5,039,057 which are both hereby incorporated by reference.

Referring to FIG. 1, the digital imaging system 100 includes an X-ray tube 106 that can be positioned in the beam path so as to project a beam of X-rays along the proton beam path through a region of a patient 108 that is positioned in front of a snout or nozzle 110 (FIG. 2) of the beam delivery system 102. An image capture device 112 is located along the path of the proton beam on the opposite side of the patient 108. The image capture device 112 includes a fluorescing screen 114 which is configured to fluoresce in response to X-rays impacting thereon.

The photons produced by the fluorescing screen are then directed along a compact path, which is described in greater detail in reference to FIGS. 5A–5D hereinbelow, to a camera 116 which then produces a digital image from the photons. The camera 116 is cooled in a manner that will be described in greater detail hereinbelow to approximately −30° C. to remove excess heat and to thereby eliminate noise in the image produced by the camera. The camera 116 is controlled by control electronics 120 and by control and synchronization logic 122 so that the shutter of the camera 116 opens in response to the X-ray tube 106 transmitting the X-rays and then captures the image which can then be provided via a net 124 to a treatment room digital imaging display workstation 126.

The treatment room digital imaging display workstation 126 produces a display on a monitor 130 of the digital image that was captured by the camera 116. Further, the treatment room digital imaging display workstation 126 receives master prescription images of the patient 108 which are simultaneously displayed on a monitor 132 in the treatment room.

As will be described in greater detail in reference to FIGS. 6 and 7 hereinbelow, the imaging system 100 of the preferred embodiment obtains a digital image of the region of the patient's body that is positioned along the path of the beam for a given position of the gantry and then displays this image on the monitor 130. The system 100 also receives a prescription master image of the patient's body, wherein a target isocenter has been defined with respect to various monuments or landmarks within the patient's body. This master prescription image displays the portion of the patient's body containing the target isocenter from the same perspective on the monitor 132, i.e., the same gantry angle, as the X-ray image that is simultaneously being displayed on the monitor 130. The treating physician then has to identify the monuments or landmarks in the X-ray image on the monitor 130 that correspond to the monuments and landmarks in the master prescription image on the monitor 132 and the treatment room digital imaging display workstation 126 then determines the spatial relation between the center of the beam in the X-ray image on the monitor 130 with the target isocenter displayed on the monitor 132. This spatial relation can then be used to move the patient in an appropriate fashion so that the patient is positioned in front of the nozzle so that the beam path intersects the target isocenter.

Figure 2:
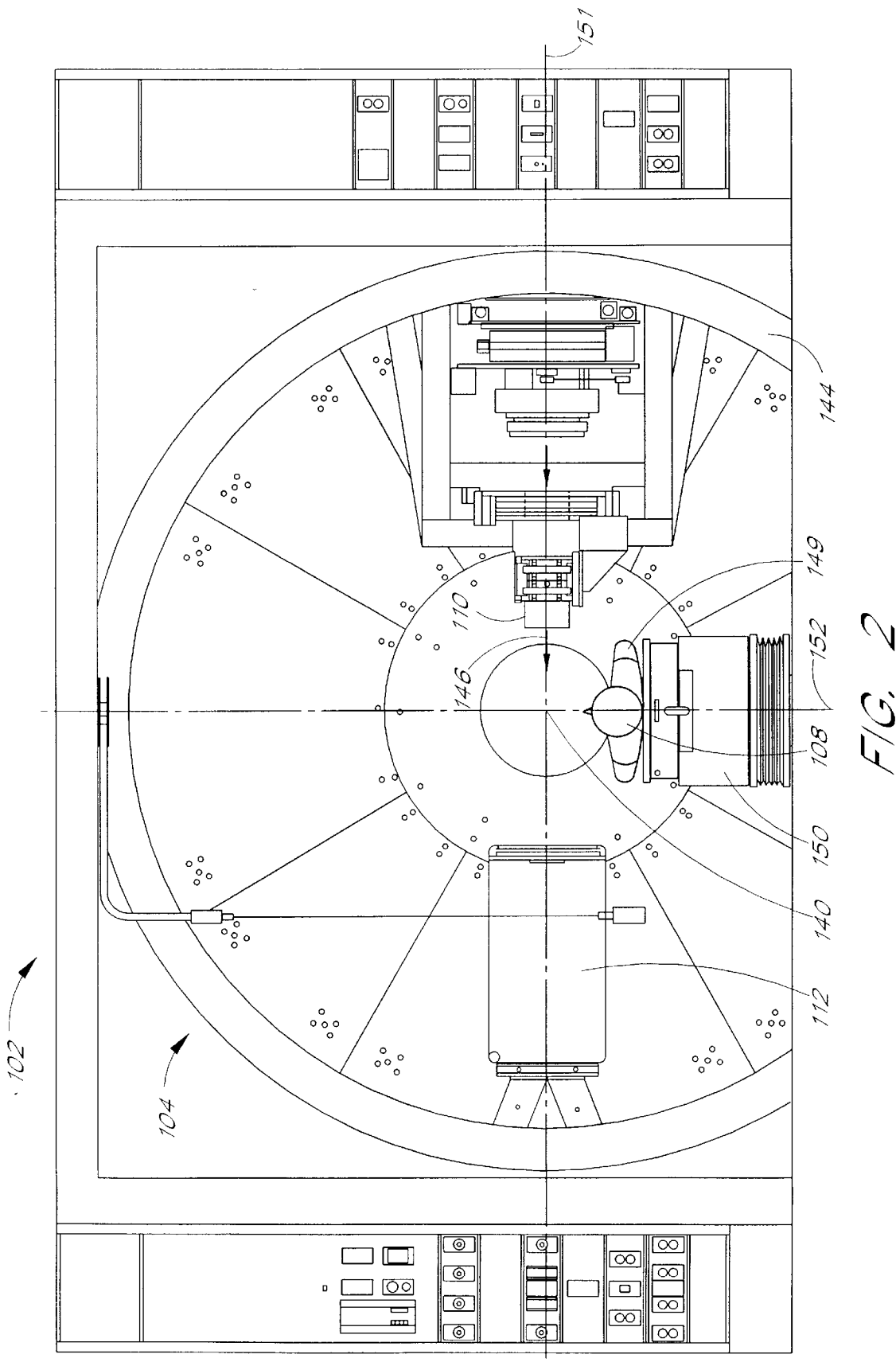
FIG. 2 is a front isometric view of a gantry for delivering a proton beam to a patient wherein the system of FIG. 1 is installed on the gantry.

FIG. 2 illustrates a preferred embodiment of the beam delivery system 102, which incorporates the imaging system 100, in greater detail. Specifically, the beam delivery system 102 includes a gantry described above which rotates about a center point 140. The beam delivery system 102 includes a snout 110 where the proton beam is emitted. Preferably, the snout is mounted on a ring (not shown) of the gantry so that the snout rotates about the center point 140. The X-ray source 106 is mounted to the beam delivery system 102 so as to be rotatable about the center point 140. Similarly, the image capture device 112 is also mounted on the ring at a position opposite the X-ray source 106 (FIG. 3) so as to be centered about the beam path 146 in all the angular orientations of the beam delivery system. In FIG. 2, the gantry 104 is positioned so that the snout would emit a beam along a beam path 146 that corresponds to an x-axis 151. It will be appreciated, however, that the snout 110 can be moved so that the beam path 146 extends in a different direction but still intersects the center point 140. The beam delivery system 102 also includes a treatment table 150 that is moveable along a z-axis 152 and the X-ray source 106.

The patient 108 is positioned in a pod 149, such as the pod disclosed in U.S. Pat. No. 4,905,267 which is hereby incorporated by reference, and the pod 149 and patient 108 are then positioned on the treatment table 150. The pod 149 is moveable with respect to the treatment table 150 along the x-axis 151 and along a y-axis that extends out of the page of the drawing in FIG. 2 and also along the z-axis and can also be rotationally aligned. The movement of the pod on the treatment table can be accomplished in any of a number of well known manners, such as positioning the pod within a cradle attached to the treatment table wherein the cradle has activators which move the pod. One possible system for moving the pod after the offset has been determined is the system that is currently in use at Loma Linda University Medical Center in Loma Linda, Calif.

Typically, the pod 149 is configured so that when the patient 108 is positioned in the pod 149, the patient 108 is in a substantially fixed orientation with respect to the pod 149. Consequently, each time the patient 108 is positioned in the pod 149, the patient's orientation to the pod 149 remains substantially the same. This then requires that the pod 149 be positioned on the table 150 so that the pod and the patient are positioned in front of the snout 110 so that the target isocenter within the patient is located within the center of the beam emanating from the snout 110.

Figure 3:
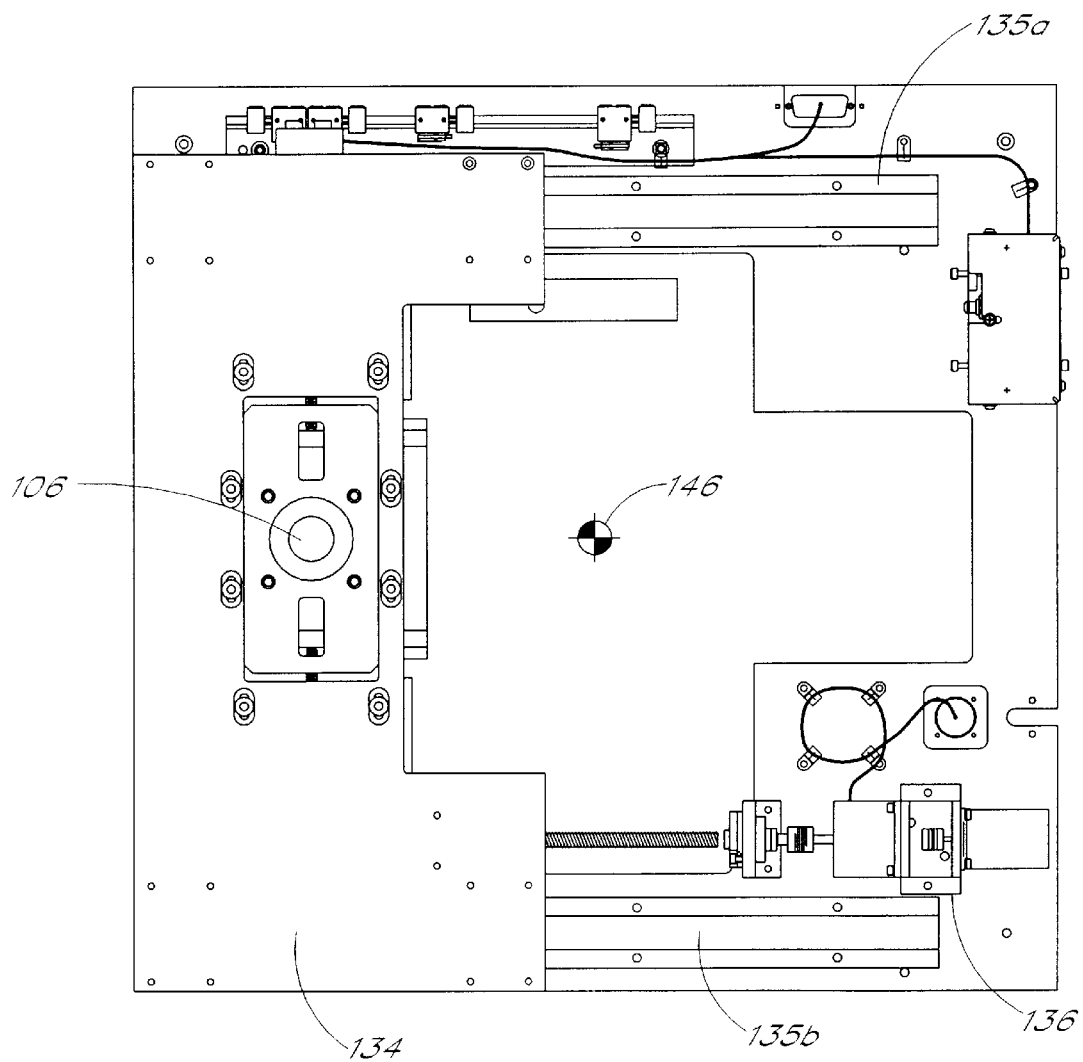
FIG. 3 is a front elevational view of a movable X-ray assembly looking upstream along the beam delivery line.

FIG. 3 is an elevational view of the X-ray source 106 of the digital imaging system 100. As shown, the X-ray source 106 is mounted to the beam delivery system 102 so that it is capable of being positioned within the beam path 146 and then removed from the beam path 146. Hence, the X-ray source 106 can project X-rays along the beam path 146 which then pass through the patient 108 who is positioned in the pod 149 on the table 150 to the image capture device 112. The X-ray source 106 is mounted on a movable sled 134 which is movable along two tracks 135a and 135b. A screw motor assembly 136 is actuated by a treatment room control system (not shown) in response to the treating physician initiating the X-ray imaging sequence in the manner that is described in greater detail hereinbelow. The screw motor assembly 136 is configured to position the sled 134 and hence the X-ray source 106 in the beam path 146 so that, when the X-ray source 106 produces X-rays, the X-rays propagate along the beam path 146. In the preferred embodiment, the X-ray source 106 is comprised of a 30–150 kVA X-ray tube manufactured by Varian Inc. of Palo Alto, Calif., Model B150 model housing a Model A192 tube. The X-ray generator and control circuitry is comprised of an Electromed International Model No. EDEC 30 general purpose X-ray generator. The generator and controller 131 are capable of inducing the screw motor assembly 136 to move the sled 134 and the X-ray source 106 into the beam path 146 and then induce the X-ray source 106 to produce an X-ray imaging beam. Once the imaging process is complete, the sled 134 and X-ray source 106 are removed from the beam path 146 to permit the treatment beam to be transported to the target isocenter.

Figure 4:
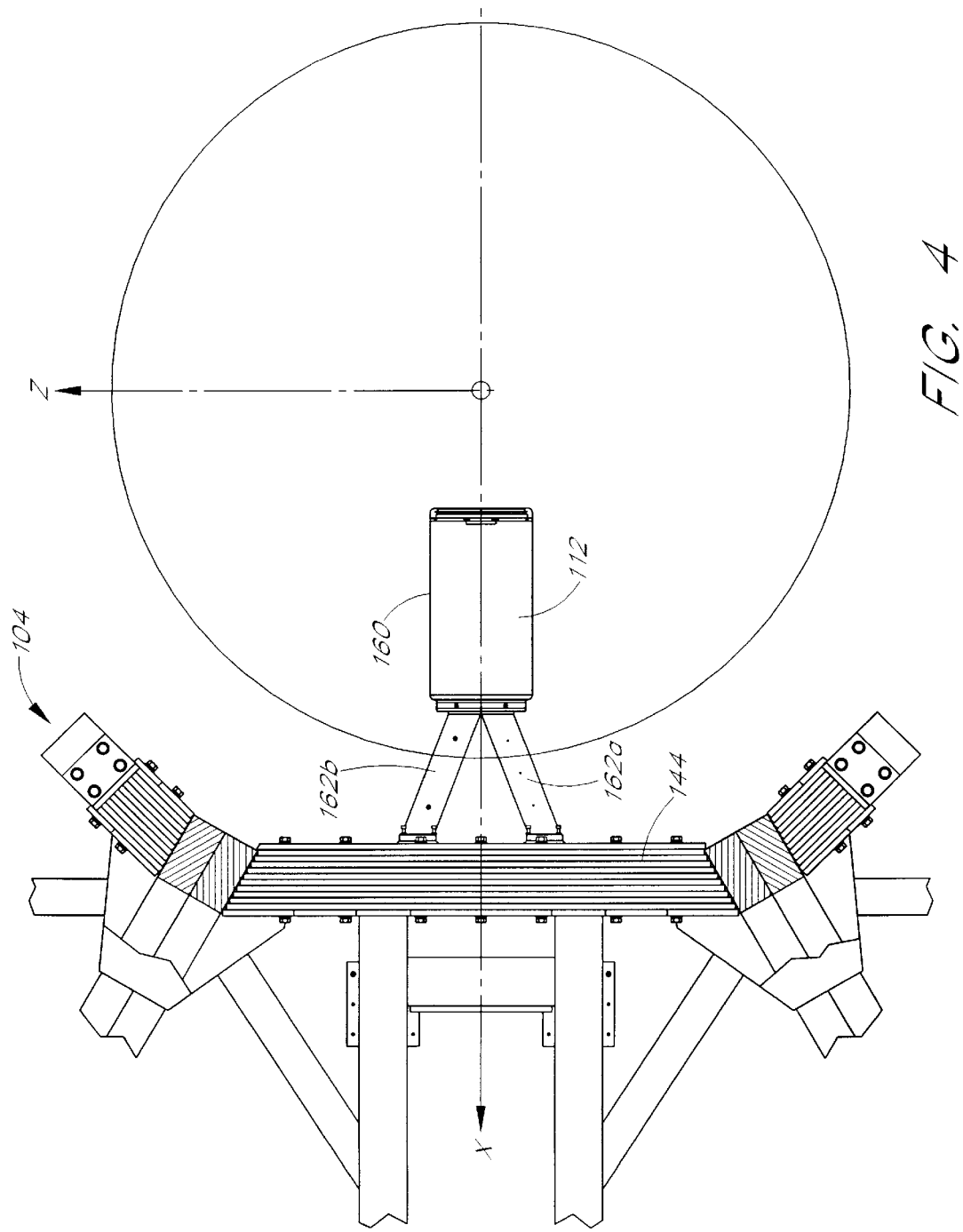
FIG. 4 is a detailed view of an image capture device of the digital imaging system of FIG. 1 mounted on a portion of the gantry of FIG. 2.

FIG. 4 is a perspective view of the image capture device 112 as it is mounted on one or more shielding plates 144 that are mounted to the gantry of the beam delivery system 102. Specifically, the image capture device 112 is housed within a rectangular enclosure 160 which is then mounted via mounting studs 162a and 162b to the interior shielding plates 144 of the gantry. As shown in FIG. 2, the image capture device is attached to the gantry so as to be positioned in the beam path 146 regardless of the rotational position of the gantry. Hence, when the X-ray source 106 is positioned within the beam path and produces X-rays, the image capture device 112 receives the X-rays as they propagate along the beam path 146 and after they have passed through the patient 108.

Hence, the X-ray source 106 and the image capture device 112 are capable of producing an image of the portion of the patient 108 that is positioned in front of the nozzle of the beam delivery system 102 in every orientation of the gantry 104. It will be appreciated that the image capture device 112 has to be mounted to the ring 144 of the gantry in a manner where the image capture device 112 will remain in the beam path 146 throughout the whole range of motion of the gantry 104. Hence, the supports 162a and 162b, as well as the enclosure 160, are made of a sufficiently rigid material so that the image capture device 112 does not move with respect to the snout 110 throughout the whole range of motion of the gantry.

Figure 5B:
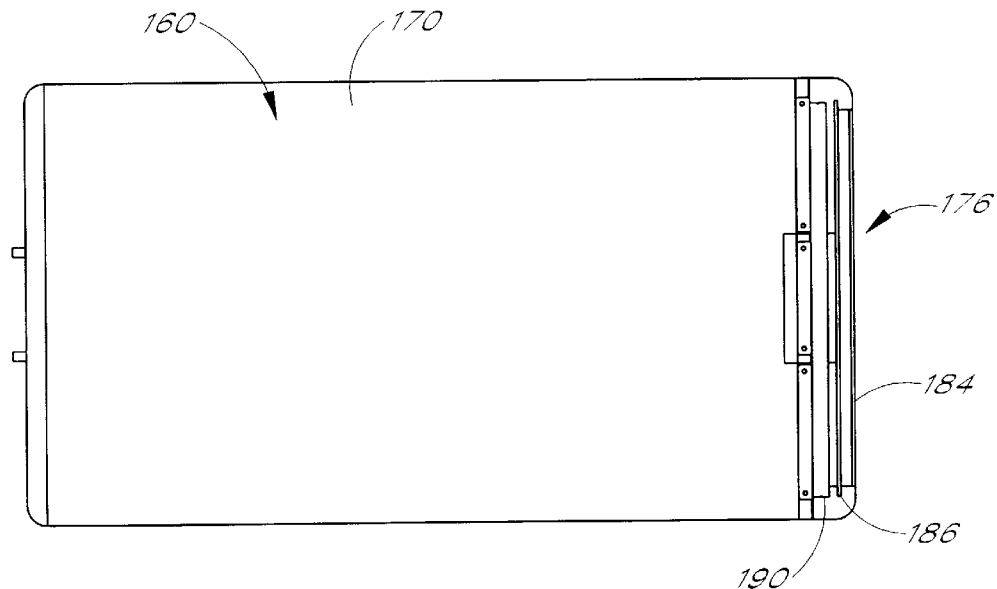

FIGS. 5A–5E illustrate the image capture device 112 in greater detail. Specifically, FIG. 5A shows the enclosure 160 of the image capture device 112 with the outer walls 170 of the enclosure partially broken away to show the components positioned therein. In the preferred embodiment, the enclosure is comprised of a frame 172 with a plurality of panels 174 bolted to the frame 172 in such a manner that the interior of the enclosure 160 is dark. It will be understood from the following discussion that the image capture device 112 must produce an accurate, undistorted digital image of the portion of the body of the patent 108 that is positioned in front of the snout 110, i.e., along the beam path 146, from X-rays produced by the X-ray source 106. Hence, the enclosure 160 must be constructed so that no additional light is introduced into the enclosure other than the light occurring as a result of X-rays impinging upon the image capture device 112 in the manner described below.

Figure 5C:
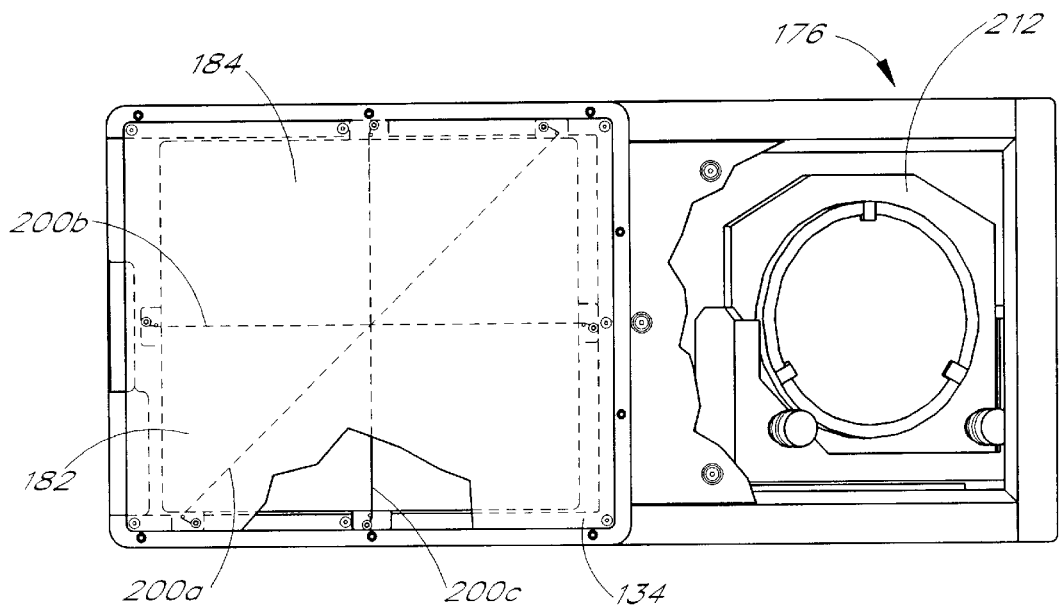

FIGS. 5B and 5C illustrate a side view and a front side 176 of the image capture enclosure 160, respectively. The front side 176 is the side which is facing the X-ray source 106 and is perpendicular to the beam path 146 (FIG. 2) when the image capture device 112 is mounted to the gantry 104 in the manner shown in FIG. 2. A square aperture or entry port 182 (FIG. 5C) is formed in the left-hand side of the front side 176 of the enclosure 160. In the preferred embodiment, there is a protective cover 184, a radiographic grid slot 186 and an X-ray cassette slot 190 positioned in front of the entry port 182. Further, there is a fluorescing screen assembly 192 (FIG. 5A) that is positioned immediately behind the X-ray cassette slot 190 so as to be positioned immediately adjacent the entry port 182 of the enclosure 160.

As shown in FIG. 5C, three cross-wires 200a–200c are formed in the protective cover so as to intersect at a point which is in the center of the entry port 182. As will be described hereinbelow, the cross-wires 200a–200c provide a visual indication to a treating physician as to the position of the center of the X-rays propagating down the beam path 146 relative to monuments within the body of the patient 108. Hence, the intersection of the cross-wires 200a–200c is preferably located at the exact center of the beam path 146. This requires the enclosure 160 of the image capture device 112 to be exactly located with respect to the snout 110.

In the preferred embodiment, the radiographic grid slot 186 and the X-ray cassette slot 190 are both capable of receiving a radiographic grid 187 and an X-ray cassette 191 (FIG. 5A). Hence, patient alignment can also be performed using the prior art technique of obtaining photographic X-ray images of the position of the patient. Hence, the patient alignment system of the preferred embodiment allows for both alignment using digital images and alignment using photographic images.

In the event that the digital image of the patient is desired, the X-ray cassette 191 (FIG. 5A) is removed from its holder so that X-rays emanating from the X-ray source 106 impinge upon the fluorescing screen assembly 192. This results in the fluorescing screen assembly 192 generating protons in the locations where the X-rays have impacted upon the fluorescing screen assembly 192. These photons generally propagate inward into the enclosure 160 in the direction of the arrow 202 (FIG. 5A) through one or more baffles 204 and towards a secondary mirror 206. In the preferred embodiment, the fluorescing screen assembly 192 is comprised of a Kodak Lanax Fast Intensifier Screen, Product No. 1476175. It consists of a 14"×14" square of gadolinium sulphur dioxide ($Gd_2O_2S$:Tb) which produces the photon in response to the X-rays impacting on the surface of the fluorescing screen 192.

The photons impinge on the secondary mirror 206 and are then reflected in the direction of arrow 210 to a primary mirror 212. Subsequently, the photons are then reflected from the primary mirror 212 in the direction of the arrow 214 to a lens 216 of the camera 116. As depicted in FIG. 5A, photons produced by X-rays impacting on the fluorescing screen assembly 192 travel in a generally Z-shaped path 203 towards the camera 116. The Z-shaped path 203 allows the enclosure 160 to be built to dimensions that are sufficiently compact to allow for installation on the gantry 104. In the preferred embodiment, the enclosure 160 is approximately 32 inches by 32 inches by 14 inches deep.

The fluorescing screen assembly 192 produces photons which are representative of the X-rays that are impacting upon the front surface of the screen 192 and the photons are then transmitted to the lens 216. Preferably, the secondary mirror is comprised of a ¼ wave flat mirror with a protected aluminum surface that is mounted at an angle of 25.5490° to the path of the protons in enclosure 160. In the preferred embodiment, the secondary mirror 206 is positioned within a fixed mount that is capable of retaining the mirror at this angle to the beam path 146 throughout the entire range of motion of the gantry 104. The primary mirror 212 is comprised of a round front surface mirror that is mounted on a two axis gimble which allows ±4° of adjustment on each axis. The primary mirror 212 is oriented so that the light reflected from the secondary mirror 206 is substantially entirely reflected into the lens 216 of the camera 116.

It will be appreciated that, since very low levels of light are being produced by the fluorescing screen assembly 192 as a result of the X-rays impacting the front surface of the fluorescing screen 192, the control of the reflected light in the enclosure 160 is an important design issue. It will also be appreciated that stray light produced by the fluorescing screen assembly 192 is typically scattered in all directions. This light is controlled in the preferred embodiment through two mechanisms.

The first mechanism is that the interior surfaces of the enclosure 160 are configured to be minimally reflective. Specifically, in the preferred embodiment the interior of the enclosure 160 and most of the components therein have been bead blasted to provide a matte finish and then black anodized. Further, the baffles 204 also trap stray light by causing stray light to reflect multiple times before reaching the camera lens and thereby losing its intensity. While, in the preferred embodiment two baffles 204 are shown, it will be appreciated that multiple baffles may be positioned within the enclosure 160 to further limit the degrading effects of stray light on any subsequent image produced by the image capture device 112. The baffles 204 are positioned so that substantially all of the light that is incident upon the lens 216 of the camera 116 is travelling in a line that is parallel to the preferred path 203 of the light in the enclosure 160. Hence, light that emanates from the fluorescing screen assembly 192 at an angle to the path 203, is preferably absorbed or reflected multiple times so that it does not reach the lens 216. In this manner, noise in any resulting digital image is reduced.

Preferably, the camera 116 is mounted to the interior of the image capture device enclosure 160 on a mount that allows for adjustment about a horizontal, vertical and longitudinal axis. Further, the mount should also allow for angular adjustment about an optical axis 214 which is defined as the path of the photons from the mirror to the lens. This allows for the camera to be oriented in an optimum position for receiving the image produced by the X-rays impinging on the fluorescent screen assembly 192. Further, the camera 116 is configured to produce an image based upon the low levels of light produced by the X-rays impinging on the fluorescing screen assembly 192.

In the preferred embodiment, the camera is a CCD camera that has 512×512 active pixels with a 100% fill factor, the objective field size of the camera is 355.6 mm×355.6 mm wherein the pixels are 0.69 mm square. Preferably, the camera is a thermally electric cooled (TEC) CCD type camera with liquid recirculation that removes the TEC generated heat. In the preferred embodiment, the camera is a model MCD 1000S scientific grade CCD camera available from Spectral Source, Inc. of Westlake Village, Calif. The lens 216 is preferably comprised of a F.95 lens with a 50 mm focal length.

Figure 5D:
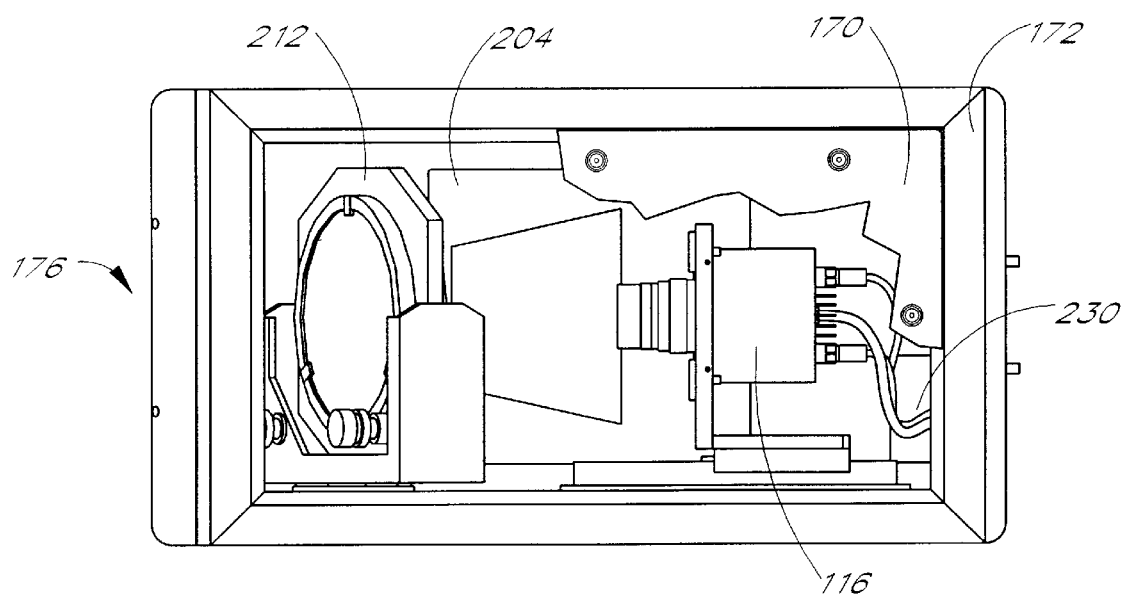
Figure 5E:
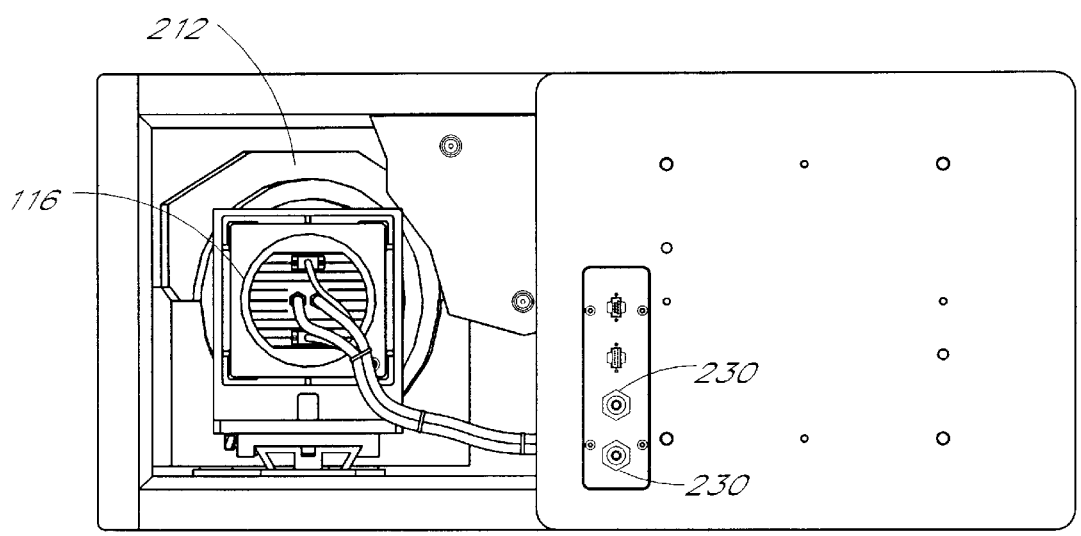

As shown in FIGS. 5D and 5E, the camera 116 is water cooled through a pair of cooling hoses 230 that provide water to the camera 116 and remove heated water from the camera 116. The cooling hoses 230 in the preferred embodiment are interconnected with a water supply (not shown) which is a component of the gantry assembly 104. The water cooling system cools the CCD camera so that the CCD camera is maintained at a −30° C. temperature. This cooling of the camera 116 ensures that the camera 116 will be able to produce a visual digital image that corresponds to an X-ray image of the portion of the patient 108 that is positioned in front of the snout 110 of the beam delivery system 102.

Figure 6:
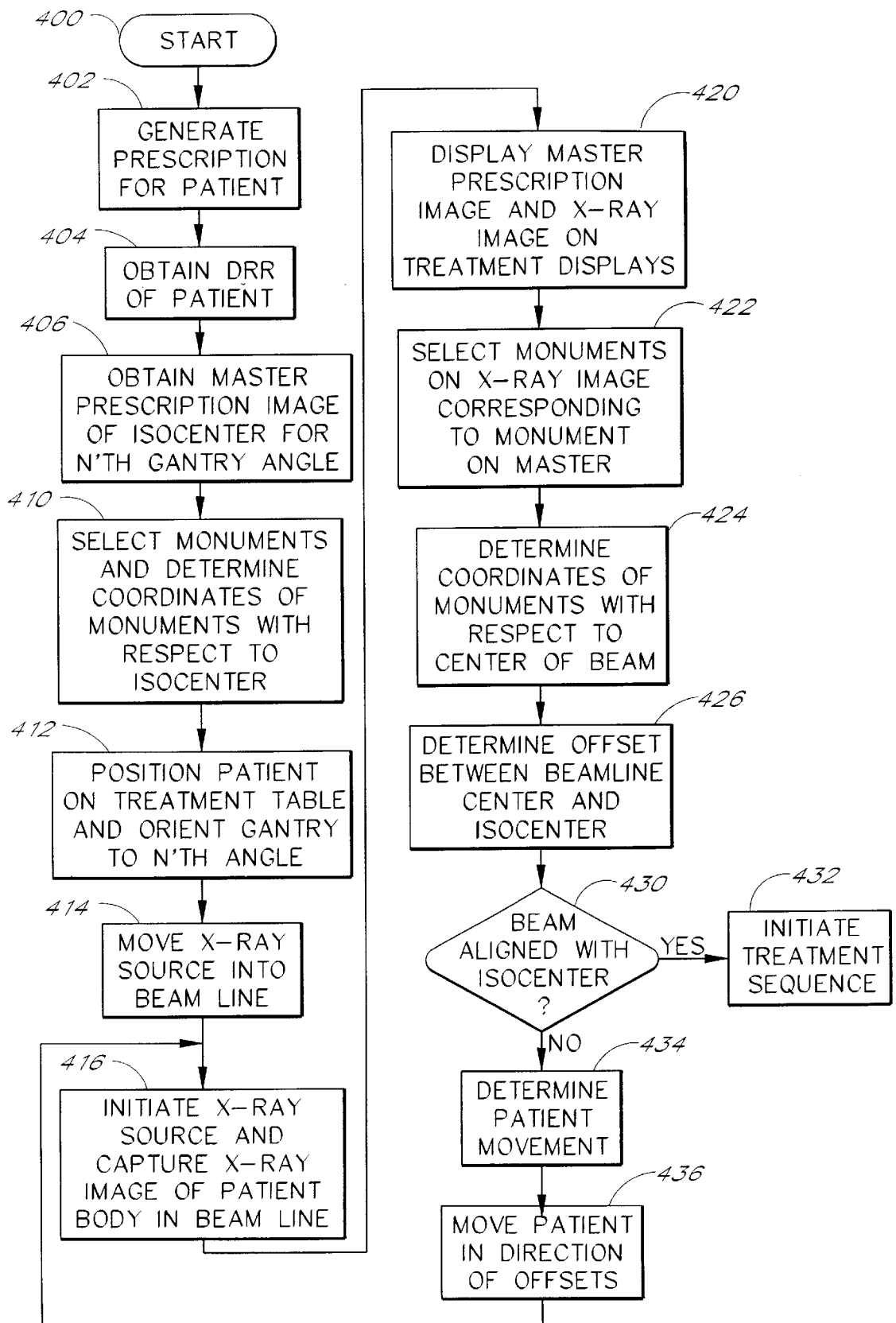
FIG. 6 is a flow chart illustrating the operation of the digital imaging system of FIG. 1.

FIG. 6 is a flow chart which illustrates the operation of the system 100 to determine the position of the patient 108 relative the snout 110 of the beam delivery system 102. Specifically, from a start state 400, a prescription for the patient is then generated in state 402 using well-known techniques. Typically, the prescription is based upon the physician determining the location, characteristics, and size of the portion of the patient's body to be treated. For example, if the treatment consists of applying radiation treatment to a tumor, the prescription will be based upon the size, characteristics and location of the tumor. The prescription will include such information as the radiation dose to be delivered to the tumor, the frequency of the radiation dose, and the angles that the radiation dose will be delivered to the patient from the gantry. This prescription is typically generated using well-known dosimetry techniques.

Figure 7A:
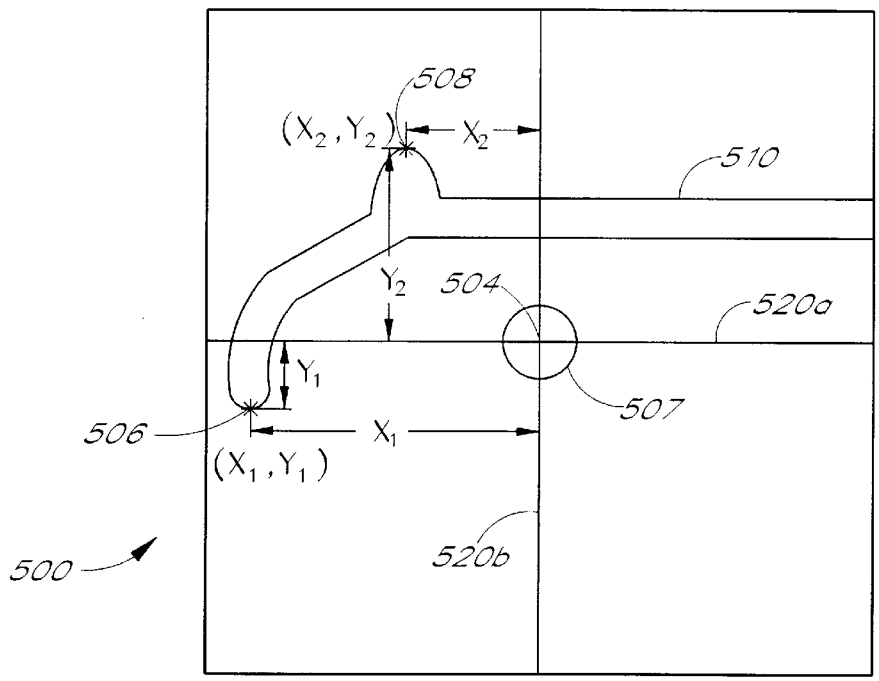
FIG. 7A is an exemplary drawing of a region of the patient's body with a target isocenter and several preselected monuments.

Further, a digitally reconstructed radiograph (DRR) is also developed for the patient in state 404 using well-known techniques. Specifically, in the preferred embodiment, DRR files are created using a DRR application using techniques described in a paper entitled "Computation of Digitally Reconstructed Radiographs for Use in Radiotherapy Treatment Designs" by George Sherouse, et al. published in the *International Journal of Radiation Oncology Biology Physics*, Vol. 18 pp 651–658, 1989 which is hereby incorporated by reference, and developed by the University of North Carolina on a Sun Spark 5 workstation. The DRR is obtained by taking a plurality of CT scans of the patient in the region of the afflicted tissue wherein the CT scans can be developed into a DRR file which displays the portion of the patient's body from any given angular perspective. The development of DRR files displaying afflicted tissue, such as a tumor, located at a target isocenter within the patient's body, is a well-known process for radiation treatment planning. Hence, a master prescription image 500 (FIG. 7A) can be generated in state 406 of a region 502 of the patient's body surrounding a target isocenter 504 from the perspective of a given gantry angle. An exemplary master prescription image 500 is shown in FIG. 7A. The image 500 in FIG. 7A has been significantly simplified for explanatory purposes.

FIG. 7A illustrates that the image 500 has a representation of the target isocenter 504 in the region 502 of the patient 108. Further, there are two rigid structures or monuments 506 and 508 on an adjacent skeletal structure 510 that have been selected by the prescribing physician. As shown in FIG. 7A, a pair of synthetic cross hairs 520a and 520b are generated so as to be centered about the target isocenter 504. The distance from the monuments 506 and 508 relative the synthetically produced cross-hairs 520a and 520b form a reference for future alignment of the patient 108 in the manner that will be described hereinbelow. A person skilled in this art will, of course, appreciate that the image of the master prescription image 500 has been significantly simplified for the purposes of clarity. In an actual master prescription image, the prescribing physician will select a plurality of monuments on the skeletal structure of the patient and will often generate master prescription images from two different perspectives to ensure that the patient is accurately aligned in all three dimensions.

Once the master prescription image 500 has been created from the DRR data, a physician can then select the monuments 506 and 508 in state 410 on the master prescription image and use these monuments to determine the coordinates of the target isocenter 502 relative to the monuments 506, 508. Preferably, the treating physician selects these monuments using the workstation 126 and the monuments generally consist of points on the patient's skeletal system 510 that will be visible on the subsequently produced digital X-ray image of the patient 108. The target isocenter 504 corresponds to the region of the afflicted tissue and, the target isocenter 504 can be identified on the master prescription image 500.

As shown in FIG. 7A, the relative position of the monuments to selected points on both the synthetic cross hairs 520a and 520b can be determined. The distance of the selected points on the cross hairs from the target isocenter 504 can also be determined. Specifically, the distances between each monument and the cross hairs 520a and 520b in a direction that is perpendicular to the cross hairs 520a and 520b can first be determined, i.e., the X and Y coordinates of the monument with respect to the target isocenter. Hence, the spatial relationship between the monuments 506 and 508 and the target isocenter 502 can be determined and defined in terms of X and Y coordinates so that the monument 506 has coordinates of $X_1$, $Y_1$ and the monument 508 has coordinates of $X_2$, $Y_2$.

Once the master prescription image 500 of the patient 108 has been developed, complete with the selection of the monuments and the determination of the vector coordinates of the target isocenter relative the monuments, this information can then be provided to the digital imaging system 100 and used for subsequent treatments of the patient 108.

Specifically, in state 412, the patient can then be positioned on the treatment table 150 (FIG. 2) and the gantry 104 can then be rotated to a desired treatment angle. As discussed above, the patient 108 is preferably substantially immobilized within the pod and the pod is positioned on the treatment table 150 in a fixed orientation relative to the snout 110 of the beam delivery system 102. Typically, the patient is positioned within the pod and the pod is positioned on the table 110 so that the pod is generally aligned with the snout 110 of the beam delivery system 102.

Subsequently, the X-ray source 106, is positioned within the beam line 146 in state 414 in the manner described in reference to FIG. 3 and, in state 416, the X-ray source is initiated so that X-rays emanate out of the snout 110 of the beam delivery system 102, through the portion of the patient's body that is located immediately in front of the snout 110 and to the image capture device 112. This results in an image 500' of the portion of the patient's body that is located immediately in front of the snout 110 of the beam delivery system 102 being generated and displayed by the workstation 126 or the display 130 (FIG. 1).

Figure 7B:
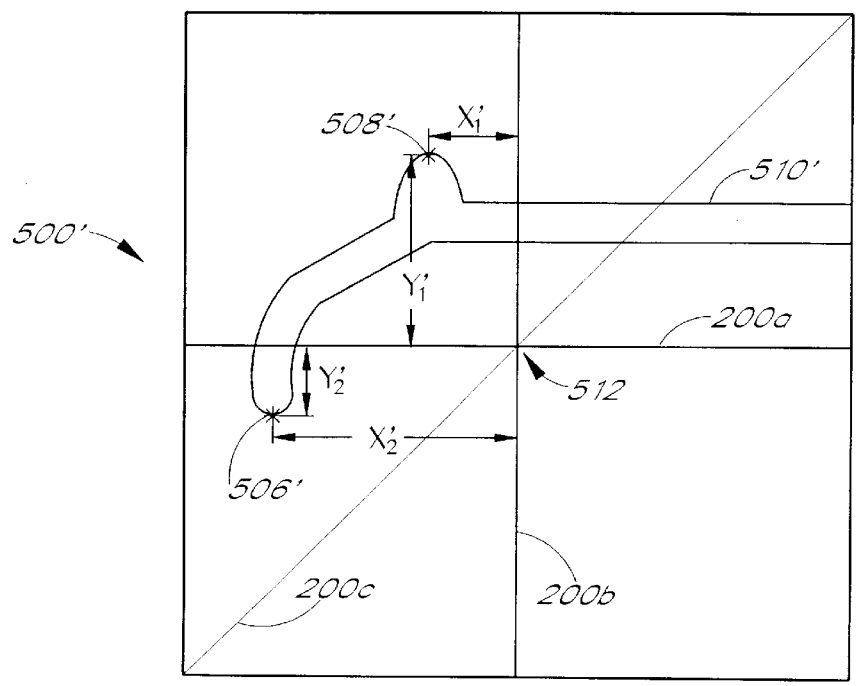
FIG. 7B is an exemplary view of an X-ray image of the portion of the patient's body in the beam path of the system of FIG. 1.

An exemplary captured X-ray image 500' is shown in FIG. 7B. This image consists primarily of the skeletal structure 510' of the patient 108 in the region that is in front of the snout 110 with the cross-wires 200a–200c (FIG. 5C) superimposed on the image. It will be appreciated that the cross-wires interrupt X-rays that are directed towards the fluorescing screen assembly 192 (FIGS. 5A and 5B) which thereby results in fewer photons being generated in the region of the cross-wires. Preferably, the cross-wires 200a–200c are positioned so that they intersect in the direct geographic center of the beam path 146. Further, there may in fact be a second set of cross-wires positioned in the beam line located adjacent the snout 110 of the beam delivery system 102 so that the two sets of cross-wires can be used for alignment verification. For example, misalignment between the two sets of cross-wires will indicate that the image capture system 102 is no longer centered about the beam path 146 which will inform the operator of the gantry system 102 to take the necessary corrective action.

Once the X-ray image 500' of the patient 108 in the beam path 146 has been captured by the image capture system 112, the image 500' is fed to the treatment room digital imaging display workstation 126 (FIG. 1) and is then displayed on the treatment room image display monitor 130. Further, the master prescription image 500 is also simultaneously displayed on the monitor 132 in state 420. This allows the treating physician to simultaneously view the master prescription image 500 of FIG. 7A and the X-ray image 500' of FIG. 7B. Subsequently, the treating physician can then, in state 422, select monuments 506' and 508' on the X-ray image 500' that correspond to the monuments 506 and 508 on the master prescription image 500. Preferably, the treating physician selects these images by using a mouse and clicking on the monuments shown on the X-ray image.

Once the monuments 506', 508' have been selected on the X-ray image 500' that correspond to the monuments 506 and 508 selected on the master prescription image 500, the workstation 126, in state 424, then determines the coordinates of the monuments 506' and 508' ($X_1'$, $Y_1'$) and ($X_2'$, $Y_2'$), respectively, on the X-ray image with respect to the beam center 512. As explained above, the beam path center 512 is indicated by the intersection of the cross-wires 200a–200c. The third cross hair 200c can also be used in a similar fashion. By comparing the coordinate values ($X_1$, $Y_1$) and ($X_2$, $Y_2$) determined with respect to the master prescription image and the coordinate values ($X_1'$, $Y_1'$) and ($X_2'$, $Y_2'$) the offset between the target isocenter 504 and the beamline center 512 can then be determined.

Hence, the computer in the display workstation 126 then determines whether the beam center 512 is aligned with the isocenter 504 in decision state 430. In the event that the beam center 512 is aligned with the isocenter 504, the digital image system 100 then enters a state 432 wherein the treatment sequence can be initiated and the patient 108 can receive the treatment beam. Typically, the treatment sequence will entail removing the X-ray source 106 from the beam path, requesting the proton beam from the beam source and providing the beam to the patient after appropriate calibration and verification has been conducted.

In the event that the beam center 512 in the X-ray image 500' is not aligned with the isocenter 504 in the master prescription image 500, the imaging system 100 then, in state 434, determines the direction the patient 108 has to move so that the isocenter 504 and the beam path center 512 are aligned. In the preferred embodiment, a least squares approximation between the coordinates of the isocenter 504 from the monuments 506 and 508 and the coordinates of the center point 512 of the X-ray image from the monuments 506' and 508' is used to determine the direction and magnitude of movement of the patient. The system 100 then moves the patient 108 in the direction of the offsets in state 436. In the preferred embodiment, the table 150 is automated so as to be movable in response to commands provided by the treating physician. Hence, the treating physician simply has to enter the movement values determined in state 434 and the table 150 moves the patient 108 who is positioned fixedly within the pod 149 to the new position. Subsequently, the X-ray source is reinitiated in state 416 and the process comprising the steps of states 416 through 430 is repeated until the isocenter 504 and the beam path center 512 correspond within an acceptable degree of error.

While in the preferred embodiment, the alignment is performed by matching monuments selected by the treating physician, other techniques can also be used for comparing the master prescription image to the x-ray image for alignment purposes. Specifically, shape recognition software can also be used that will identify the monuments in the x-ray image so that these monuments will not have to be specifically highlighted by the treating physician. Further, curve recognition software wherein the target isocenter can be defined with respect to a bone structure or monument having a specific curving outline. Subsequently, the same curving structure can then be identified by the computer in the x-ray image and the position of the center of the beam line can be determined with respect to the same bone structure having the specific curving outline. This information can then be used to determine the offset between the center of the beam and the target isocenter for subsequent adjustment of the position of the patient. Consequently, a person of ordinary skill in the art will appreciate that the monuments used to determine the offsets between the center of the beam and the target isocenter do not have to be designated by the prescribing physician but can be identified by computer software and the monuments do not necessarily have to comprise particular points on the skeletal structure but can consist of entire bone structures such as curving bones and the like.

Hence, the digital imaging system of the preferred embodiment provides for more efficient alignment of the patient with the beam nozzle. Specifically, the treating physician simply has to position the patient in the pod in front of the nozzle and the iteratively determine the relative position between the beam path and the target isocenter relative to selected monuments within the patient's body. This eliminates the need for producing photographic X-ray images of the portion of the patient's body in front of the nozzle and also allows for automatic calculation of the offset between the beam path center and the target isocenter. Consequently, patient alignment is simplified and is more efficient which allows for greater use of the treatment facility.

Although the foregoing description of the preferred embodiment of the present invention has shown, described and pointed out the fundamental novel features of the invention, it will be understood that various omissions, substitutions and changes in the form of the detail of the apparatus as illustrated, as well as the uses thereof, may be made by those skilled in the art without departing from the spirit of the present invention. Consequently, the scope of the invention should not be limited to the foregoing discussion, but should be defined by the appended claims.

What is claimed is:

1. An imaging system for a proton beam therapy system having a proton source, a beam delivery system with a nozzle that is mounted on a gantry so that said proton beam can be delivered to the patient from a plurality of angles, wherein said proton beam therapy system receives a master prescription image of a region of a patient that is to be treated, said imaging system comprising:

an imaging beam source mounted on said beam delivery system wherein said imaging beam source is movable between a first position, wherein said imaging source can project an imaging beam along a treatment beam path towards a first side of said patient, and a second position wherein said imaging source is removed from said beam path to thereby allow said proton beam to travel along said treatment path;

an imaging beam receiver attached to said gantry so that said receiver is centered about said beam path throughout a plurality of angles of orientation of the gantry wherein said receiver receives said imaging beam after it has passed through a region of the patient that is positioned in said beam path;

an image capture device proximate to said receiver, wherein said image capture device directly receives a non-intensified signal from said receiver and produces a patient orientation image of the region of the patient's body that is positioned in said beam path; and a controller which receives both said master prescription image and said patient orientation image, wherein said controller is configured so that one or more rigid structures can be designated on said master prescription image so as to define the relative position of an isocenter to be treated in the patient's body with respect to said one or more rigid structures and wherein said controller is also configured so that said one or more rigid structures can be designated on said patient orientation image so that said controller can determine the relative location of the center of said beam line with respect to said one or more rigid structures and wherein said controller using said relative position of said target isocenter and said beam line center with respect to said one or more rigid structures determine the relative movement between the patient and the gantry required so that the position of the center of the beam line with respect to the one or more rigid structures corresponds to the position of the target isocenter with respect to said one or more rigid structures.

2. The system of claim 1, wherein said imaging beam source is comprised of an X-ray source that is mounted so as to be movable in a direction that is transverse to the direction of the proton beam path.

3. The system of claim 2, wherein said imaging beam receiver is comprised of a fluorescing screen that is positioned in said beam path wherein said fluorescing screen produces photons in response to X-rays impinging upon said fluorescing screen.

4. The system of claim 3, wherein said image capture device is comprised of a CCD camera that receives said photons produced by said fluorescing screen and thereby produces said patient orientation image.

5. The system of claim 4, wherein said CCD camera is water cooled so as to remove excess noise from said patient orientation image.

6. The system of claim 5, wherein said receiver and said CCD camera are positioned in an enclosure wherein said receiver is positioned within an aperture of said enclosure that is centered about said beam path and wherein said enclosure defines a path for said photons produced by said receiver which directs said photons to said CCD camera.

7. The system of claim 6, wherein said enclosure includes two mirrors so that said photons emanating from said fluorescing screen travel in a first direction towards one of said mirrors, are reflected in a second direction towards a second mirror and are then reflected in a third direction, which is generally parallel to said first direction, towards said CCD camera.

8. The system of claim 7, wherein said enclosure includes one or more baffles to prevent at least a portion of any photons which are travelling in a direction that has a component transverse to the directions of said path from reaching said CCD camera.

9. The system of claim 8, wherein said X-ray source is comprised of a diagnostic quality X-ray tube that operates in the 30 kV–150 kV energy range, the fluorescing screen is comprised of a square of gadolinium sulphur dioxide and the CCD camera includes a thinned CCD sensor that is 512 by 512 pixels and said CCD camera includes a F.95 lens with a 50 mm focal length.

10. The system of claim 9, wherein said CCD camera receives said photons directly from said fluorescing screen in said path so that said patient orientation image is substantially undistorted by intensification.

11. The system of claim 4, further comprising a pair of cross-wires attached to said receiver so as to be centered in said beam path, wherein said cross-wires interrupt said X-rays from said X-ray source so that fewer photons are produced by said fluorescing screen in the region of said cross-wires which results in an image of said cross-wires appearing on said patient orientation image.

12. The system of claim 1, further comprising:

a first monitor which receives signals from said controller and displays said master prescription image; and a second monitor which receives signals from said controller and displays said patient orientation image wherein a treating physician can manipulate said controller so as to designate said one or more rigid structures on said patient orientation image.

13. The system of claim 1, wherein said controller performs a least squares approximation to determine the offset between the center of the beam line and the isocenter relative said one or more rigid structures and wherein said one or more rigid structures comprise monuments on said patient's skeletal structure.

14. An imaging system for a proton beam therapy system having a proton source, a beam delivery system with a nozzle that is mounted on a gantry so that said proton beam can be delivered to the patient from a plurality of angles, wherein said imaging system receives a master prescription image of a region of the patient that is to be treated, said imaging system comprising:

an X-ray source mounted on said beam delivery system wherein said X-ray source is movable between a first position, wherein said source can project an X-ray beam along a treatment beam path towards a first side of said patient, and a second position wherein said source is removed from said beam path to thereby allow said proton beam to travel along said treatment path;

an X-ray beam receiver attached to said gantry so that said receiver is centered about said beam path throughout the plurality of angles of orientation of the gantry wherein said receiver receives said X-ray beam after it has passed through a region of the patient that is positioned in said beam path and produces a photon image corresponding to the portion of the patient's body in the beam line;

an image capture device which receives said photon image directly from said X-ray beam receiver, and produces a patient orientation image of the region of the patient's body that is positioned in said beam path so that said patient orientation image is substantially undistorted by intensification; and a controller which receives both said master prescription image and said patient orientation image, wherein said controller is configured so that one or more monuments can be designated on said master prescription image so as to define the relative position of an isocenter to be treated in the patient's body with respect to said one or more monuments and wherein said controller is also configured so that said one or more monuments can be designated on said patient orientation image so that said controller can determine the relative location of the center of said beam line with respect to said one or more monuments and wherein said controller using said relative position of said target isocenter and said beam line center with respect to said one or more monuments determines the movement of the patient required so that the position of the center of the beam line with respect to the one or more monuments corresponds to the position of the target isocenter with respect to said one or more monuments.

15. The system of claim 14, further comprising a pair of cross-wires attached to said receiver so as to be centered in said beam path, wherein said cross-wires interrupt said X-rays from said source so that fewer photons are produced by said X-ray receiver in the region of said cross-wires which results in an image of said cross-wires appearing on said patient orientation image.

16. The system of claim 14, wherein said controller uses the relative position of the target isocenter and the relative position of the center of said beam line with respect to said one or more monuments to perform a least squares approximation to determine the direction and magnitude of movement of the patient with respect to the beam line so that the target isocenter is positioned at the center of the beam line.

17. The system of claim 14, further comprising:

a first monitor which receives signals from said controller and displays said master prescription image; and a second monitor which receives signals from said controller and displays said patient orientation image wherein a treating physician can manipulate said controller so as to designate said one or more monuments on said patient orientation image.

18. The system of claim 14, wherein said X-ray receiver is comprised of a fluorescing screen that is positioned in said beam path wherein said fluorescing screen produces photons in response to X-rays impinging upon said fluorescing screen.

19. The system of claim 18, wherein said image capture device is comprised of a CCD camera that receives said photons produced by said fluorescing screen and thereby produces said patient orientation image.

20. The system of claim 19, wherein said CCD camera is water cooled so as to remove excess noise from said patient orientation image.

21. The system of claim 20, wherein said receiver and said CCD camera are positioned in an enclosure wherein said receiver is positioned within an aperture of said enclosure that is centered about said beam path and wherein said enclosure defines a path for said photons produced by said receiver which directs said photons to said CCD camera.

22. The system of claim 21, wherein said enclosure includes two mirrors so that said photons emanating from said fluorescing screen travel in a first direction towards one of said mirrors, are reflected in a second direction towards a second mirror and are then reflected in a third direction, which is generally parallel to said first direction, towards said CCD camera.

23. The system of claim 22, wherein said enclosure includes one or more baffles to prevent photons which are travelling in a direction that has a component transverse to the direction of said path from reaching said CCD camera.

24. The system of claim 23, wherein said X-ray source is comprised of a diagnostic quality X-ray tube that operates in the 30 kV–150 kV energy range, the fluorescing screen is comprised of a square of gadolinium sulphur dioxide and the CCD camera includes a thinned CCD sensor that is 512 by 512 pixels and said CCD camera includes a F.95 lens with a 50 mm focal length.

25. A method of aligning a patient in a proton beam therapy system so that the center of a beam line from a nozzle is centered at a target isocenter positioned within the body of the patient, said method comprising the steps of:

obtaining a master prescription image of the patient for a desired orientation of the beam wherein the master prescription image is stored in a computer system;

positioning the patient on a treatment table so that the region of the patient's body containing the target isocenter is positioned in front of the nozzle;

transmitting an imaging beam along the treatment beam path so that the imaging beam is transmitted into the region of the patient's body positioned in front of the nozzle;

receiving the imaging beam after it has been transmitted into the region of the patient's body and directly capturing a non-intensified patient orientation image of the region of the patient's body that is positioned in said beam path that is provided to said computer system;

designating said one or more monuments, using said computer system, on said master prescription image;

designating said one or more monuments, using said computer system, on said patient orientation image wherein said one or more monuments designated on both said master prescription image and said patient orientation image correspond to the same point of said patient's anatomy;

determining the relative position of the center of said treatment beam with respect to the one or more monuments designated in the patient orientation image;

determining the offset between the target isocenter with respect to the one or more monuments in the master prescription image and the center of the beam with respect to the one or more monuments in the patient orientation image using said computer system; and determining the distance and direction the patient will have to be moved so that the position of the center of the beam with respect to the one or more monuments coincides with the position of the target isocenter with respect to the one or more monuments.

26. The method of claim 25, wherein the step of transmitting an imaging beam along the treatment beam path comprises the steps of:

positioning an X-ray source in the treatment beam path; and inducing the X-ray source to emanate X-rays along the treatment beam path.

27. The method of claim 26, wherein the step of receiving the imaging beam comprises receiving X-rays after the X-rays have traveled along the treatment beam path through said patient.

28. The method of claim 27, wherein the step of receiving the imaging beam and capturing a patient orientation image comprises the steps of:

positioning a fluorescing screen in said beam path so that photons are produced in response to the X-rays of said X-ray beam impacting said fluorescing screen;

directing said photons along a compact path to a CCD camera.

29. The method of claim 28, further comprising the step of positioning a pair of cross-wires so as to be centered about the center of the treatment beam path so that a resulting image of the cross-wires appears in said patient orientation image at a point representative of the center treatment beam path.

30. The method of claim 25, wherein the steps of selecting the one or more monuments comprises the steps of:

displaying a digital image of said master prescription image on a display;

manipulating a user input device to a monument on the skeletal structure of said patient displayed on said display;

manipulating said user input device to select said monument;

displaying a digital image of said patient orientation image on a display;

manipulating a user input device to said monument on the skeletal structure of said patient displayed on said display; and manipulating said user input device to select said monument.

31. The method of claim 30, further comprising the step of:

calculating the relative location between the selected monument in the master prescription image and the target isocenter in said master prescription image; and calculating the relative location between the selected monument in the patient orientation image and the center of said beam line.

32. The method of claim 25, wherein the step of determining the distance and direction the patient will have to be moved comprises performing a least squares fit between the relative location of the target isocenter with respect to said one or more monuments of the master prescription image and the relative location of the center of the beam path with respect to said one or more monuments.

33. A therapeutic imaging system for a treatment beam therapy system having a treatment beam source, a beam delivery system with a nozzle that is configured to provide the treatment beam from a plurality of different angles, said therapeutic imaging system comprising:

an X-ray beam source mounted on said beam delivery system wherein said X-ray beam source is movable between a first position, wherein said X-ray source can project an X-ray beam along a treatment beam path towards a first side of said patient, and a second position wherein said X-ray is removed from said beam path to thereby allow said treatment beam to travel along said treatment beam path;

a fluorescing screen positioned so as to be centered about said beam path wherein said fluorescing screen receives said X-ray beam after it has passed through a region of the patient that is positioned in said beam path and produces a resulting photon image; and a digital camera which receives said photon image directly from said fluorescing screen and produces a patient orientation image of the region of the patient's body that is positioned in said beam path so that said patient orientation image is substantially undistorted by intensification.

34. The system of claim 33, wherein said therapeutic imaging system is configured to be used with a proton beam therapy system having a proton source, a beam delivery system with a nozzle that is mounted on a gantry so that said proton beam can be delivered to the patient from a plurality of angles and wherein said therapeutic imaging system is capable of producing said patient orientation image over a plurality of orientations of said gantry.

35. The system of claim 34, further comprising a controller which receives a master prescription image of a region of a patient that is to be treated and said patient orientation image wherein said controller is configured so that one or more monuments can be designated on said master prescription image so as to define the relative position of an isocenter to be treated in the patient's body with respect to said one or more monuments.

36. The system of claim 35, wherein said controller is also configured so that said one or more monuments can be designated on said patient orientation image so that said controller can determine the relative location of the center of said beam line with respect to said one or more monuments and wherein said controller using said relative positions of said target isocenter and said beam line center with respect to said one or more monuments determines the relative movement between the patient and the nozzle required so that the position of the center of the beam line with respect to the one or more monuments corresponds to the position of the target isocenter with respect to said one or more monuments.

* * * * *